US009546991B2

(12) United States Patent
Li et al.

(10) Patent No.: US 9,546,991 B2
(45) Date of Patent: Jan. 17, 2017

(54) SYSTEM FOR THE CONCOMITANT ASSESSMENT OF DRUG DISSOLUTION, ABSORPTION AND PERMEATION AND METHODS OF USING THE SAME

(71) Applicant: Absorption Systems Group, LLC, Exton, PA (US)

(72) Inventors: Jibin Li, West Chester, PA (US); Ismael J. Hidalgo, Exton, PA (US)

(73) Assignee: Absorption Systems Group, LLC, Exton, PA (US)

(*) Notice: Subject to any disclaimer, the term of this patent is extended or adjusted under 35 U.S.C. 154(b) by 0 days.

(21) Appl. No.: 14/946,998

(22) Filed: Nov. 20, 2015

(65) Prior Publication Data

US 2016/0146774 A1    May 26, 2016

Related U.S. Application Data

(60) Provisional application No. 62/082,738, filed on Nov. 21, 2014.

(51) Int. Cl.
*C12M 1/34* (2006.01)
*G01N 33/15* (2006.01)
(Continued)

(52) U.S. Cl.
CPC ............. *G01N 33/15* (2013.01); *G01N 13/00* (2013.01); *G01N 33/5008* (2013.01);
(Continued)

(58) Field of Classification Search
CPC ....... C12M 25/02; C12M 25/04; C12M 21/08; C12M 23/06; C12M 25/14; C12M 27/02; G01N 15/0806; G01N 2015/086; G01N 2013/00; G01N 2013/003; G01N 2013/006; G01N 13/04; G01N 1/4005; G01N 2001/4016; G01N 33/15; G01N 13/00; G01N 13/15; G01N 13/5082; G01N 13/5008; B01D 63/087; B01D 69/10; B01D 6/28

See application file for complete search history.

(56) References Cited

U.S. PATENT DOCUMENTS

| 3,749,646 A * | 7/1973 | Pirt ........................ C12M 23/08 |
| | | 210/321.84 |
| 3,802,272 A * | 4/1974 | Bischoff ................ G01N 13/00 |
| | | 366/142 |

(Continued)

FOREIGN PATENT DOCUMENTS

| WO | WO 96/02627 A1 | 2/1996 |
| WO | WO 97/16717 A1 | 5/1997 |

(Continued)

OTHER PUBLICATIONS

"The Dissolution Procedure: Development and Validation", The United States Pharmacopeial Convention, May 2012, Chapter USP 35, 675-681.

(Continued)

*Primary Examiner* — William H Beisner
(74) *Attorney, Agent, or Firm* — Baker & Hostetler LLP

(57) ABSTRACT

Disclosed herein are devices for assessing drug dissolution, absorption and permeation, the devices comprising a chamber, a permeability barrier, and a securing cap, each in fluid communication with each other. The chamber comprises a reservoir and an extension. The permeability barrier is configured to hold cells, tissues, or artificial membranes, and the securing cap is configured to reversibly attach to the permeability barrier or the extension of the chamber. Also provided are systems for assessing drug dissolution, absorption and permeation, the systems comprising at least one of the devices for assessing drug dissolution, absorption and permeation, a dissolution vessel configured to hold a disso- (Continued)

lution medium, and a stirring apparatus within the dissolution vessel. Methods for concomitant measuring of dissolution, absorption and/or permeation of a drug are also provided.

29 Claims, 5 Drawing Sheets

(51) Int. Cl.
| | |
|---|---|
| *G01N 13/00* | (2006.01) |
| *G01N 33/50* | (2006.01) |
| *C12M 3/00* | (2006.01) |
| *C12M 1/12* | (2006.01) |
| *C12M 1/06* | (2006.01) |

(52) U.S. Cl.
CPC ......... *G01N 33/5082* (2013.01); *C12M 21/08* (2013.01); *C12M 23/06* (2013.01); *C12M 25/02* (2013.01); *C12M 25/14* (2013.01); *C12M 27/02* (2013.01); *G01N 2013/006* (2013.01)

(56) References Cited

U.S. PATENT DOCUMENTS

| | | | |
|---|---|---|---|
| 4,335,438 A | 6/1982 | Smolen | |
| 4,450,076 A * | 5/1984 | Medicus | B01D 61/28 210/242.1 |
| 4,863,696 A * | 9/1989 | Saydek | G01N 13/00 210/232 |
| 5,110,473 A * | 5/1992 | Hassett | B01D 61/246 210/295 |
| 6,022,733 A | 2/2000 | Tam et al. | |
| 6,217,772 B1 * | 4/2001 | Alam | B01D 17/0217 210/232 |
| 7,331,251 B2 | 2/2008 | Das et al. | |
| 7,470,545 B2 | 12/2008 | Hughes | |

FOREIGN PATENT DOCUMENTS

| | | |
|---|---|---|
| WO | WO 2010/049447 A1 | 5/2010 |
| WO | WO 2010/089619 A1 | 8/2010 |

OTHER PUBLICATIONS

Aoyagi et al., "Preparation of a polymer containing hexadecylpyridinium bromide groups and its utilization as a transdermal drug penetration enhancer", Polymer, Jan. 1, 1991, vol. 32, No. 11, 2106-2111.
Chen et al., "A monolithic polymeric microdevice for pH-responsive drug delivery", Biomedical Microdevices, Aug. 12, 2009, vol. 11, No. 6, 1251-1257.
Galia et al., "Evaluation of Various Dissolution Media for Predicting In Vivo Performance of Class I and II Drugs", Pharmaceutical Research, May 1998, 15, 5, 698-705.
Hidalgo et al., "A new side-by-side diffusion cell useful for studying transport across epithelial cell monolayers", In Vitro Cell. Dev. Biol., Sep.-Oct. 1992, 28A, 578-580.
Hidalgo et al., "Characterization of the unstirred water layer in Caco-2 cell monolayers using a novel diffusion apparatus", Pharmaceutical Research, 1991, 8, 2, 2-7.
Kataoka et al., "In vitro system to evaluate oral absorption of poorly water-soluble drugs: simultaneous analysis on dissolution and permeation of drugs", Pharmaceutical Research, Oct. 2003, 20, 10, 1674-1680.
Kim et al., "Terahertz dynamic imaging of skin drug absorption", Optics Express, Apr. 23, 2012, vol. 20, No. 9, 9476-9484.
Kuhfeld et al., "In vitro measurement of drug transport using a new diffusion chamber compatible with Millicell culture supports: performance with caco-2 monolayers", International Journal of Pharmaceutics, Jan. 1, 1996, vol. 133, 47-58.
Nicolaides et al., "Biorelevant dissolution testing to predict the plasma profile of lipophilic drugs after oral administration", Pharmaceutical Research, 2001, 18, 380-388.
Petersen et al., "Evaluation of alkylmaltosides as intestinal permeation enhancers: Comparison between rat intestinal mucosal sheets and Caco-2 monolayers", European Journal of Pharmaceutical Sciences, Nov. 1, 2012, vol. 47, No. 4, 701-712.
Tsinman et al., "Dissolution-Permeability Apparatus with Integrated In Situ Concentration Monitoring of both Donor and Receiver Compartments", Pion Inc., 2013, 1 page.
Tycho, "Prediction of Formulation-dependent Food Effects for Poorly Water Soluble Compounds using the In Vitro Dissolution-Permeability Assay System", presented at AAPS National Meeting, Novartis Pharmaceutical Corp., Novartis Institutes for BioMedical Research, Inc., Nov. 11, 2013, 1 page.
Ussing et al., "Active transport of sodium as the source of electric current in the short-circuited isolated frog skin", Acta Physiol Scand., 1951, 23, 110-127.

* cited by examiner

SYSTEM FOR THE CONCOMITANT ASSESSMENT OF DRUG DISSOLUTION, ABSORPTION AND PERMEATION AND METHODS OF USING THE SAME

CROSS REFERENCE TO RELATED APPLICATIONS

This application claims priority to U.S. Provisional Application No. 62/082,738, filed Nov. 21, 2014, the disclosure of which is hereby incorporated by reference in its entirety.

TECHNICAL FIELD

The disclosure relates to the field of drug dissolution and permeation/absorption. In particular, disclosed herein are devices, systems, and methods for simultaneous measurement of drug dissolution, absorption and permeation across cell, tissue or artificial membranes.

BACKGROUND

For most clinical indications, the oral route of drug administration is not only the most convenient but is also associated with higher patient compliance. In the vast majority of cases, orally administered drug products must disintegrate and dissolve in the stomach before permeating the mucosal membranes of the stomach and intestines to reach the systemic circulation. Since key determinants of intestinal absorption (i.e. solubility, dissolution and permeability) are extremely difficult to obtain in vivo, especially in humans, in vitro tools to evaluate these parameters are necessary. Although there are in vitro techniques that independently permit the determination of permeability of the drug substance and the dissolution rate of the final drug product, there is currently no generally accepted scientific method for integrating both the dissolution rate and permeability data to predict the potential outcome in humans.

SUMMARY

Disclosed herein are devices for assessing drug dissolution, absorption and permeation, comprising a chamber, a permeability barrier, and a securing cap. The chamber comprises: a reservoir having a bottom, at least one side wall, and a hollow interior, the side wall having an opening; and an extension having at least one side wall, a distal end, a proximal end, and a hollow interior, wherein the distal end and the proximal end are open, and wherein the proximal end is attached to the side wall at the opening. The permeability barrier comprises at least one side wall, an open distal end, and a proximal end, and is configured to hold cells, tissues, or artificial membranes. The proximal end of the permeability barrier is configured to contact the distal end of the extension. The securing cap has at least one side wall, a distal end, a proximal end, and a hollow interior, wherein the distal end and proximal end are open. The securing cap is configured to reversibly attach to the permeability barrier or the extension. The securing cap, permeability barrier, and chamber are in fluid communication. The device can further comprise a seal configured for insertion between the distal end of the extension and the proximal end of the permeability barrier, wherein the seal is in fluid communication with the securing cap, permeability barrier, and chamber.

Also disclosed are systems for assessing drug dissolution, absorption and permeation. The disclosed systems comprise: at least one of the devices for assessing drug dissolution, absorption and permeation; a dissolution vessel configured to hold a dissolution medium; and a stirring apparatus within the dissolution vessel, wherein the system is configured to assess: dissolution rates of an intact drug tablet, capsule, or other formulation, or portions of the tablet, capsule, or other formulation; absorption of active ingredients from the tablet, capsule, or other formulation, or a portion of the tablet, capsule, or other formulation; and/or membrane permeability of active ingredients from the tablet, capsule, or other formulation, or a portion of the tablet, capsule, or other formulation. In some embodiments, the system can further comprise a lid.

Methods for concomitant measuring of dissolution, absorption and/or permeation of a drug are also provided. The methods comprise: adding an intact drug tablet, capsule, or other formulation, or a portion of the drug tablet, capsule, or other formulation, to the dissolution vessel of any one of the disclosed systems, wherein the dissolution vessel contains a dissolution medium and the device contains a permeability medium, and wherein the permeability barrier contains a layer of cells, a layer of tissue, or a layer of an artificial membrane; mixing the dissolution medium; withdrawing a sample from the dissolution vessel, the device, or both; and analyzing the sample from the dissolution vessel, the device, or both.

BRIEF DESCRIPTION OF THE DRAWINGS

The summary, as well as the following detailed description, is further understood when read in conjunction with the appended drawings. For the purpose of illustrating the disclosed devices, systems, and methods, there are shown in the drawings exemplary embodiments of the devices, systems, and methods; however, the devices, systems, and methods are not limited to the specific embodiments disclosed. In the drawings.

DETAILED DESCRIPTION OF ILLUSTRATIVE EMBODIMENTS

Figure 1:
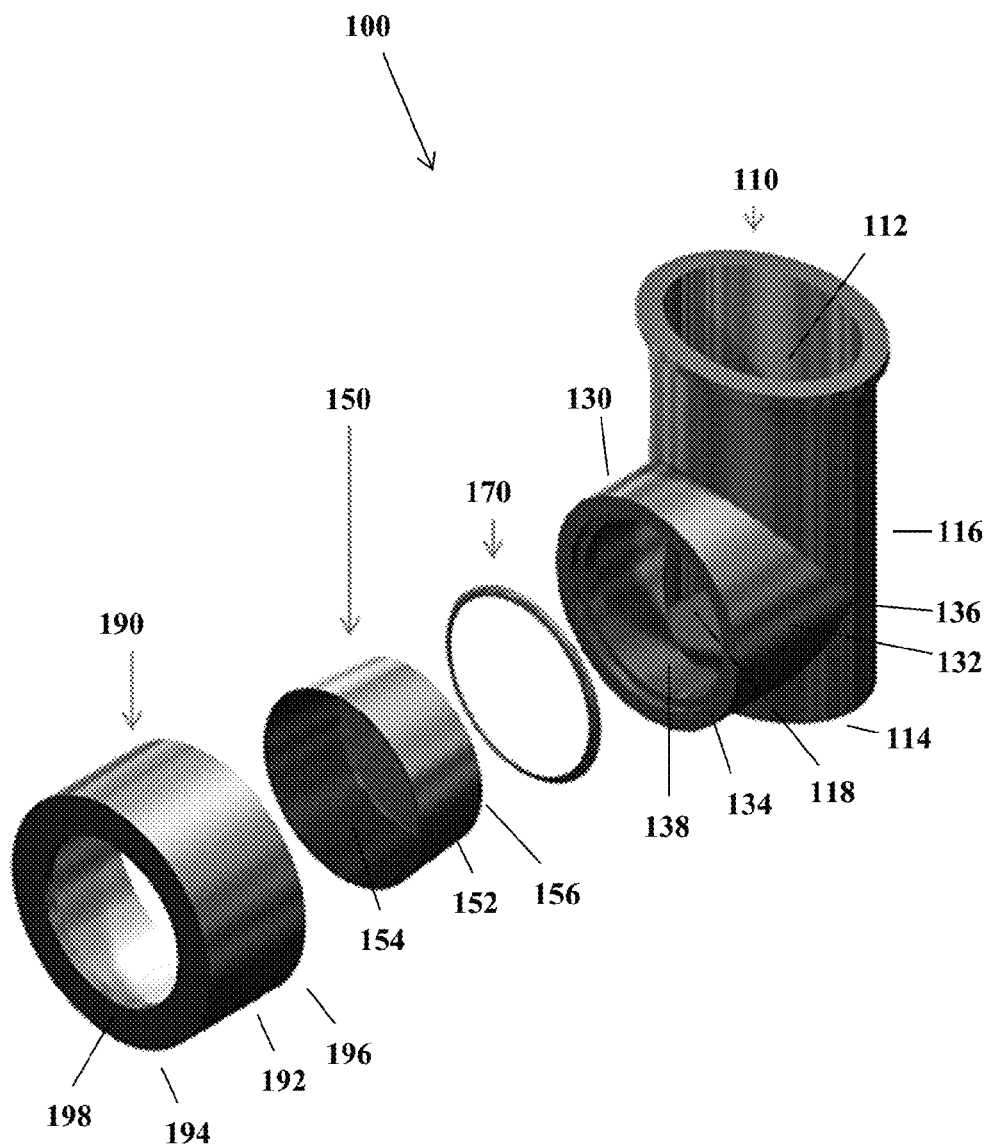
FIG. 1 illustrates the component parts of an exemplary device for assessing drug dissolution, absorption, and permeation.

The disclosed devices, systems, and methods may be understood more readily by reference to the following detailed description taken in connection with the accompanying figures, which form a part of this disclosure. It is to be understood that the disclosed devices, systems, and methods are not limited to the specific devices, systems, and methods described and/or shown herein, and that the terminology used herein is for the purpose of describing particular embodiments by way of example only and is not intended to be limiting of the claimed devices, systems, and methods.

Similarly, unless specifically otherwise stated, any description as to a possible mechanism or mode of action or reason for improvement is meant to be illustrative only, and the disclosed devices, systems, and methods are not to be constrained by the correctness or incorrectness of any such suggested mechanism or mode of action or reason for improvement.

When a range of values is expressed, another embodiment includes from the one particular value and/or to the other particular value. Further, reference to values stated in ranges include each and every value within that range. All ranges are inclusive and combinable. When values are expressed as approximations, by use of the antecedent "about," it will be understood that the particular value forms another embodiment. Reference to a particular numerical value includes at least that particular value, unless the context clearly dictates otherwise.

It is to be appreciated that certain features of the disclosed devices, systems, and methods which are, for clarity, described herein in the context of separate embodiments, may also be provided in combination in a single embodiment. Conversely, various features of the disclosed devices, systems, and methods that are, for brevity, described in the context of a single embodiment, may also be provided separately or in any subcombination.

As used herein, the singular forms "a," "an," and "the" include the plural.

Various terms relating to aspects of the description are used throughout the specification and claims. Such terms are to be given their ordinary meaning in the art unless otherwise indicated. Other specifically defined terms are to be construed in a manner consistent with the definitions provided herein.

The term "about" when used in reference to numerical ranges, cutoffs, or specific values is used to indicate that the recited values may vary by up to as much as 10% from the listed value. Thus, the term "about" is used to encompass variations of ±10% or less, variations of ±5% or less, variations of ±1% or less, variations of ±0.5% or less, or variations of ±0.1% or less from the specified value.

As used herein, "fluid communication" refers to the ability of liquids to flow between the component parts of the device—namely, the securing cap, permeability barrier, seal, and chamber.

As used herein, "other formulation" includes formulations in the form of liquids, solids, suspensions, or gels.

The disclosed systems can also be referred to as in vitro dissolution absorption systems (IDAS).

Devices for Assessing Drug Dissolution, Absorption, and Permeation

Disclosed herein are devices for assessing drug dissolution, absorption and permeation. In some embodiments, the devices for assessing drug dissolution, absorption and permeation, comprise a chamber, a permeability barrier, and a securing cap. In some embodiments, the devices for assessing drug dissolution, absorption and permeation consist of a chamber, a permeability barrier, and a securing cap. In some embodiments, the devices for assessing drug dissolution, absorption and permeation consist of a chamber, a permeability barrier, a seal, and a securing cap. In some embodiments, the devices for assessing drug dissolution, absorption and permeation consist essentially of a chamber, a permeability barrier and a securing cap. In some embodiments, the devices for assessing drug dissolution, absorption and permeation consist essentially of a chamber, a permeability barrier, a seal, and a securing cap. The chamber comprises: a reservoir having a bottom, at least one side wall, and a hollow interior, the side wall having an opening; and an extension having at least one side wall, a distal end, a proximal end, and a hollow interior, wherein the distal end and the proximal end are open, and wherein the proximal end is attached to the side wall at the opening. The permeability barrier comprises at least one side wall, an open distal end, and a proximal end, and is configured to hold cells, tissues, or artificial membranes. The proximal end of the permeability barrier is configured to contact the distal end of the extension. The securing cap has at least one side wall, a distal end, a proximal end, and a hollow interior, wherein the distal end and proximal end are open. The securing cap is configured to reversibly attach to the permeability barrier or extension. The securing cap, permeability barrier, and chamber are in fluid communication. The device can further comprise a seal configured for insertion between the distal end of the extension and the proximal end of the permeability barrier, wherein the seal is in fluid communication with the securing cap, permeability barrier, and chamber.

An exemplary device for assessing drug dissolution, absorption and permeation 100 is illustrated in FIG. 1. The device comprises a chamber 110 comprising a reservoir 112 having a bottom 114 and at least one side wall 116, the side wall having an opening 118, and an extension 130 having at least one side wall 132, a distal end 134, a proximal end 136, and a hollow interior 138, wherein the distal end 134 and the proximal end 136 are open, and wherein the proximal end 136 is attached to the side wall 116 of the reservoir 112 at the opening 118. The device also comprises a permeability barrier 150 having at least one side wall 152, an open distal end 154, and a proximal end 156, wherein the permeability barrier 150 is configured to hold cells, tissues, or artificial membrane and the proximal end 156 of the permeability barrier 150 is configured to contact the distal end 134 of the extension 130. An optional seal 170 is configured for insertion between the distal end 134 of the extension 130 and the proximal end 156 of the permeability barrier 150. The device can further comprise a securing cap 190 having at least one side wall 192, a distal end 194, a proximal end 196, and hollow interior 198, wherein the distal end 194 and proximal end 196 are open and wherein the securing cap 190 is configured to reversibly attach to the extension 130. The securing cap 190, permeability barrier 150, seal 170, and chamber 110 are in fluid communication.

The permeability barrier is configured to hold cells, tissues, or artificial membranes. In some embodiments, the permeability barrier is configured to hold a tissue layer (layer of tissue). For prediction of drug absorption in a human, human intestinal tissue (more specifically intestinal mucosa) is most relevant. Thus, in some aspects, the permeability barrier is configured to hold a human intestinal tissue. In some aspects, the human intestinal tissue is an intestinal mucosa. In addition, intestinal tissues from animals can also be assessed using the disclosed device and system, including tissues from mouse, rat, rabbit, dog, pig, monkey, etc.

In other embodiments, the permeability barrier is configured to hold a layer of cells (cell layer). The layer of cells can be a mature cell monolayer grown on a porous membrane. Thus, the permeability barrier can be configured to hold a mature cell monolayer grown on a porous membrane. In some aspects, the layer of cells can be a confluent cell monolayer. The permeability barrier can be configured to hold adherent cells. Suitable adherent cells include, but are not limited to, epithelial cells such as C2BBel cells (a sub clone of Caco-2 cells), MDCK cells, MDR-MDCK cells, BCRP-MDCK cells, Caco-2 cells, HT-29 cells, T-84 cells, or any combination thereof. In some aspects, the permeability barrier is configured to hold a layer of C2BBel cells. In some aspects, the permeability barrier is configured to hold a layer of MDCK cells. In some aspects, the permeability barrier is configured to hold a layer of MDR-MDCK cells. In some aspects, the permeability barrier is configured to hold a layer of BCRP-MDCK cells. In some aspects, the permeability barrier is configured to hold a layer of Caco-2 cells. In some aspects, the permeability barrier is configured to hold a layer of HT-29 cells. In some aspects, the permeability barrier is configured to hold a layer of T-84 cells.

In other embodiments, the permeability barrier is configured to hold a layer of artificial membrane (artificial membrane layer). The layer of artificial membrane can be prepared from porous membrane treated with lipid solutions, such as lecithin, 1,2-dioleoyl-sn-glycero-3-phosphocholine (DOPC), or phospholipid mixture.

When a layer of tissue, layer of cells, or a layer of artificial membrane is present within the permeability barrier, an interface is formed between the inside and outside of the device (i.e. between the reservoir of the chamber and the outside of the cap). Accordingly, the device enables drug permeation to be assessed across the cell, tissue, or artificial membrane layer during the drug dissolution process.

The disclosed devices are configured to receive a permeability medium. An assembled device with a tissue layer, cell layer, or artificial membrane layer in the permeability barrier, for example, is configured to receive and hold permeability medium within the chamber, as the permeability barrier containing a tissue layer, a cell layer, or an artificial membrane layer would prevent the passage of liquids out of the device. Thus, when the device is assembled and contains a layer of tissue, cells, or artificial membrane, "configured to receive" is synonymous with "configured to hold."

Suitable permeability media can contain, for example, calcium chloride ($CaCl_2$), potassium chloride (KCl), potassium phosphate monobasic ($KH_2PO_4$), magnesium chloride ($MgCl_2$), magnesium sulfate ($MgSO_4$), sodium chloride (NaCl), sodium bicarbonate ($NaHCO_3$), sodium phosphate dibasic ($Na_2HPO_4$), glucose, bovine serum albumin (BSA), or any combination thereof. In some embodiments, the permeability medium can be a buffer solution. Suitable buffer solutions include, for example, Hanks Balanced Salt Solution (HBSS). In some aspects, the HBSS can contain about 1.26 mM calcium chloride ($CaCl_2$), about 5.33 mM potassium chloride (KCl), about 0.44 mM potassium phosphate monobasic ($KH_2PO_4$), about 0.50 mM magnesium chloride ($MgCl_2$), about 0.41 mM magnesium sulfate ($MgSO_4$), about 138 mM sodium chloride (NaCl), about 4.00 mM sodium bicarbonate ($NaHCO_3$), about 0.30 mM sodium phosphate dibasic ($Na_2HPO_4$), about 25 mM glucose, and can be supplemented with about 4.5% bovine serum albumin (BSA).

Suitable pH for the permeability medium include from about pH 6.0 to about pH 8.0. In some embodiments, the pH of the permeability medium can be around about pH 7.4. In aspects where the permeability medium is a buffer solution, the medium can be adjusted so that its pH is within 0.05 unit of 7.4. In some aspects, the pH of the permeability medium can be adjusted with HEPES (4-(2-hydroxyethyl)-1-piperazineethanesulfonic acid).

The device can be configured to receive a maximum volume of from about 3 mL to about 10 mL of permeability medium. The device can be configured to receive a maximum volume of from about 4 mL to about 10 mL of permeability medium. The device can be configured to receive a maximum volume of from about 5 mL to about 10 mL of permeability medium. The device can be configured to receive a maximum volume of from about 6 mL to about 10 mL of permeability medium. The device can be configured to receive a maximum volume of from about 7 mL to about 10 mL of permeability medium. The device can be configured to receive a maximum volume of from about 8 mL to about 10 mL of permeability medium. The device can be configured to receive a maximum volume of from about 9 mL to about 10 mL of permeability medium.

The device can be configured to receive a maximum volume of about 3 mL of permeability medium. The device can be configured to receive a maximum volume of about 4 mL of permeability medium. The device can be configured to receive a maximum volume of about 5 mL of permeability medium. The device can be configured to receive a maximum volume of about 6 mL of permeability medium. The device can be configured to receive a maximum volume of about 7 mL of permeability medium. The device can be configured to receive a maximum volume of about 8 mL of permeability medium. The device can be configured to receive a maximum volume of about 9 mL of permeability medium. The device can be configured to receive a maximum volume of about 10 mL of permeability medium.

The at least one side wall, distal end, and proximal end of the extension, at least one side wall, distal end, and proximal end of the permeability barrier, at least one side wall, distal end, and proximal end of the securing cap, and the optional seal can have a number of shapes including, but not limited to, circular, oval, square, rectangular, triangular, pentagonal, hexagonal, heptagonal, octagonal, nonagonal, decagonal, and so on. In some embodiments, the distal end of the extension, the distal and/or proximal end of the permeability barrier, and the proximal end of the securing cap can have shapes that are sufficiently similar to one another, such that when the device is assembled, the proximal end of the securing cap attaches tightly to the distal end of the permeability barrier, which in turn attaches tightly to the distal end of the extension, or the proximal end of the securing cap attaches tightly to the distal end of the extension. In embodiments in which a seal is present in the device, the seal can have a shape that is sufficiently similar to the distal end of the extension, the distal and/or proximal end of the permeability barrier, and the proximal end of the securing cap, such that when the device is assembled, the seal forms a tight barrier between the distal end of the extension and the proximal end of the permeability barrier. The proximal end of the securing cap can attach tightly to the distal end of the permeability barrier, which in turn attaches tightly to the distal end of the extension, or the proximal end of the securing cap attaches tightly to the distal end of the extension. In embodiments where the extension and permeability barrier are circular, for example, the seal can be circular. In some aspects, the seal can be an O-ring. In some aspects, the seal can be multiple O-rings. In embodiments where the extension and permeability barrier are a shape other than circular, the seal can have a similar shape. For example, in some embodiments where the extension and permeability barrier are square, the seal can be square. Suitable shapes of the seal include, but are not limited to, circular, oval, square, rectangular, triangular, pentagonal, hexagonal, heptagonal, octagonal, nonagonal, and decagonal.

The at least one side wall, distal end, and proximal end of the extension, permeability barrier, securing cap, and/or optional seal can have a different shape from the remaining components of the device. For example, and without intending to be limiting, the at least one side wall 116 of the reservoir 112 can have a shape that is different from the shape of the at least one side wall 132 of the extension 130.

The inner surface of the various components of the devices can have the same shape or a different shape from the outer surface of the component. For example, and without intending to be limiting, the inner surface of the at least one side wall 132 of the extension 130 can be round, while the outer surface of the at least one side wall 132 of the extension 130 can be square.

Figure 2:
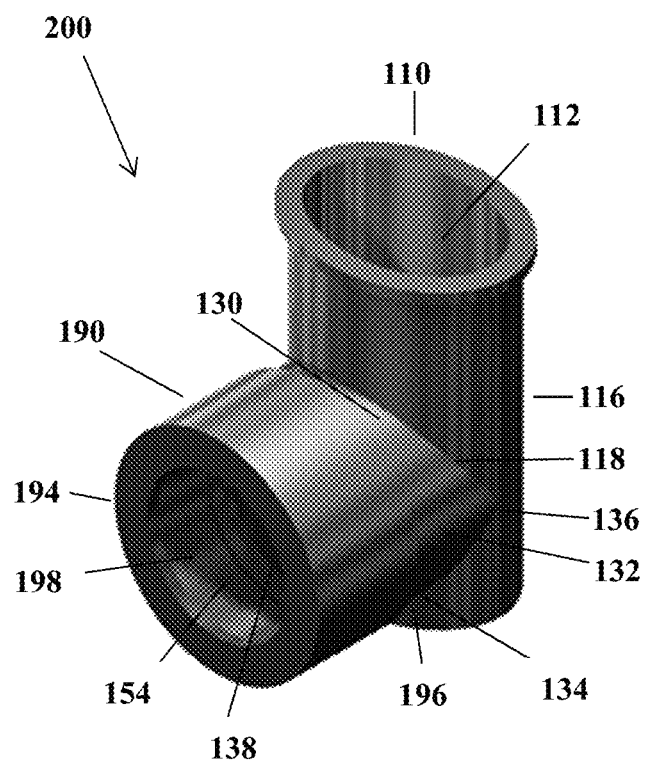
FIG. 2 illustrates an exemplary assembled device for assessing drug dissolution, absorption, and permeation.

FIG. 2 illustrates an exemplary assembled device 200 wherein the component parts have shapes that are sufficiently similar to one another. The assembled device 200 comprises a chamber 110 comprising a reservoir 112 having at least one side wall 116 with an opening 118, and an extension 130 having at least one side wall 132, a distal end 134, a proximal end 136, and a hollow interior 138, wherein the proximal end 136 is attached to the side wall 116 of the reservoir 112 at the opening 118. A securing cap 190 having a distal end 194, a proximal end 196, and hollow interior 198, is attached to the distal end 134 of the extension 130. A permeability barrier (not labeled) and seal (not labeled) rest between the securing cap 190 and the distal end 134 of the extension 130. The openings of the distal end 194 and proximal ends 196 of the securing cap 190, the distal end 154 of the permeability barrier, the seal, and the distal end 134 of the extension 130 are aligned such that the securing cap 190, permeability barrier, seal, and chamber 110 are in fluid communication.

In some embodiments, the proximal end of the permeability barrier can be configured to attach to the distal end of the extension and the proximal end of the securing cap can be configured to attach to the distal end of the permeability barrier. In other embodiments, the proximal end of the securing cap can be configured to attach to the distal end of the extension, and the permeability barrier can be configured to rest between the securing cap and the extension, such that the securing cap surrounds the permeability barrier.

In some embodiments, the distal end of the securing cap, the distal end of the permeability barrier, or both can have shapes that are sufficiently similar to the shape of the distal end of the extension, the optional seal, the proximal end of the permeability barrier, and the proximal end of the securing cap. For example, all components can be circular. In other aspects, all components can be square. In other embodiments, the distal end of the securing cap, the distal end of the permeability barrier, or both can have shapes that are different from those of the distal end of the extension, the optional seal, the proximal end of the permeability barrier, and the proximal end of the securing cap. In such embodiments, the components are assembled similarly to that described above for FIG. 2, such that the openings of the securing cap, the permeability barrier, the optional seal, and the extension are aligned and in fluid communication.

It is preferable that the top of the reservoir is open or is capable of being opened. In some embodiments, the top of the reservoir is open. The entire top of the reservoir can be open, such that the top opening has approximately the same dimension as the hollow interior of the reservoir. For example, in aspects where the reservoir is circular, the top opening of the reservoir can be circular and can have an approximately equal diameter as the hollow interior of the reservoir. In aspects where the reservoir is square, the top opening of the reservoir can be square and can have an approximately equal width on both the x and y axis as the opening of the reservoir. Alternatively, only a portion of the top of the reservoir can be open. For example, the top of the reservoir can be about 95% open, 90% open, 80% open, 70% open, 60% open, 50% open, 40% open, 30% open, 20% open, 10% open, or less than 10% open. In other embodiments, the top of the reservoir is capable of being opened. In some aspects, for example, the top of the reservoir can have a cap or lid that can be removed or opened to expose the hollow interior of the reservoir.

In some embodiments, the extension can be perpendicular to the reservoir. Thus, the angle between the extension and the reservoir can be about 90°. In other embodiments, the extension can be other than perpendicular to the reservoir. Thus, the angle between the extension and the reservoir can be greater than, or less than, 90°.

The devices and components thereof can be made from any material that is capable of holding, and being submersed in, liquid. Suitable materials include, but are not limited to, acrylic, poly(methyl methacrylate), glass, plastic, steel, metal, or any combination thereof.

Systems for Assessing Drug Dissolution, Absorption, and Permeation

Also disclosed herein are systems for assessing drug dissolution, absorption and permeation. The disclosed systems can comprise: at least one of the devices for assessing drug dissolution, absorption and permeation disclosed above; a dissolution vessel configured to hold a dissolution medium; and a stirring apparatus within the dissolution vessel, wherein the system is configured to assess: dissolution rates of an intact drug tablet, capsule, or other formulation, or a portion of the tablet, capsule, or other formulation; absorption of active ingredients from the tablet, capsule, or other formulation, or a portion of the tablet, capsule, or other formulation; and/or membrane permeability of active ingredients from the tablet, capsule, or other formulation, or a portion of the tablet, capsule, or other formulation. In some embodiments, the disclosed systems can consist of: at least one of the devices for assessing drug dissolution, absorption and permeation disclosed above; a dissolution vessel configured to hold a dissolution medium; a stirring apparatus within the dissolution vessel, and a lid, wherein the system is configured to assess: dissolution rates of an intact tablet, capsule, or other formulation, or portions of the tablet, capsule, or other formulation; absorption of active ingredients from the tablet, capsule, or other formulation, or portions of the tablet, capsule, or other formulation; and/or membrane permeability of active ingredients from the tablet, capsule, or other formulation, or portions of the tablet, capsule, or other formulation. In some embodiments, the disclosed systems can consist essentially of: at least one of the devices for assessing drug dissolution, absorption and permeation disclosed above; a dissolution vessel configured to hold a dissolution medium; a stirring apparatus within the dissolution vessel, and a lid, wherein the system is configured to assess: dissolution rates of an intact tablet, capsule, or other formulation, or portions of the tablet, capsule, or other formulation; absorption of active ingredients from the tablet, capsule, or other formulation, or portions of the tablet, capsule, or other formulation; and/or membrane permeability of active ingredients from the tablet, capsule, or other formulation, or portions of the tablet, capsule, or other formulation.

Figure 3:
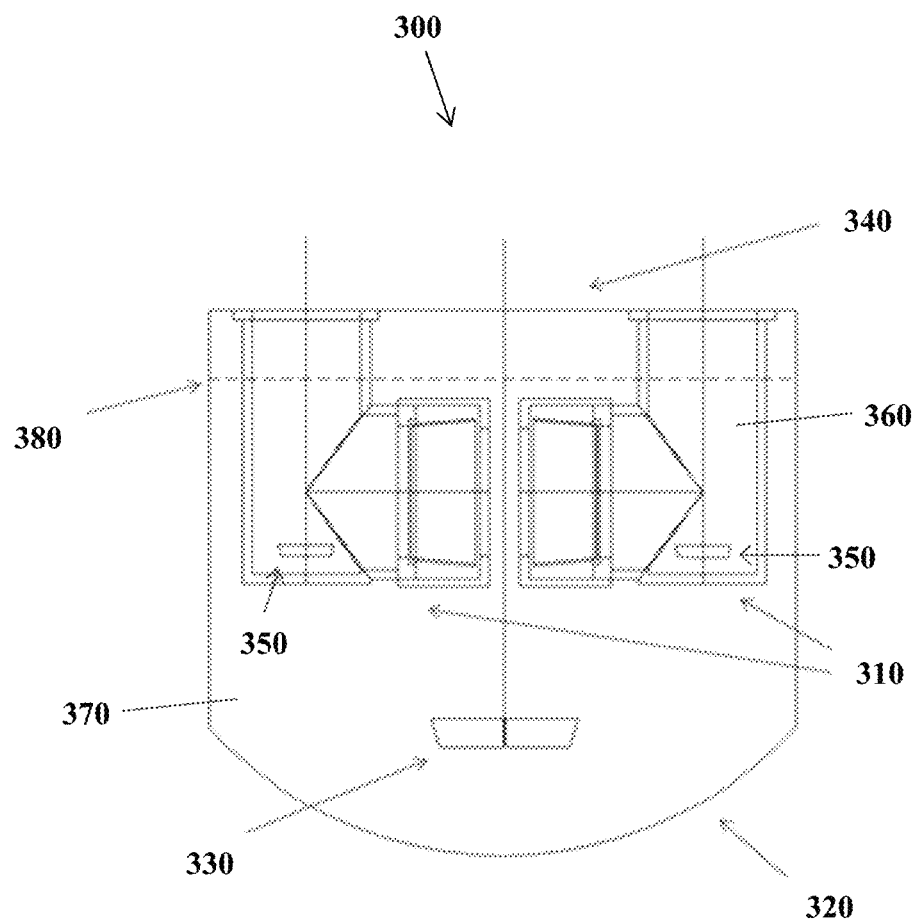
FIG. 3 illustrates an exemplary system for assessing drug dissolution, absorption, and permeation in which two devices are attached to the lid.

An exemplary system for assessing drug dissolution, absorption and permeability is illustrated in FIG. 3. The system 300 comprises: at least one device for assessing drug dissolution and absorption 310; a dissolution vessel 320 configured to hold a dissolution medium 370; a stirring apparatus 330 within the dissolution vessel 320; and a lid 340. The at least one device 310 is configured to hold a permeability medium 360. In some embodiments, the at least one device 310 can have a stirring blade 350 within the reservoir. The level of dissolution medium 370 and permeability medium 360 can be approximately equal 380. In some embodiments, the at least one device 310 can be configured to be attached to the lid 340.

Numerous stirring apparatuses are known in the art. In some embodiments, the stirring apparatus within the dissolution vessel can be a stirring blade. In other embodiments, the stirring apparatus within the dissolution vessel can be a stirring cage configured to hold the drug tablet, capsule, or other formulation. In yet other embodiments, the stirring apparatus within the dissolution vessel can be a magnetic stirring bar. In some aspects, for example, the stirring apparatus can be a magnetic stirring bar and the system can be placed on a stirring plate.

The dissolution vessel is configured to hold a dissolution medium. The dissolution medium can be a buffer solution. Suitable dissolution media include, for example, aqueous buffers described in The United States Pharmacopeial Convention, Chapter USP35, The Dissolution Procedure: Development and Validation, (2012) p. 675-681. Dissolution media can include: dilute hydrochloric acid, buffers in the physiologic pH range of 1.2 to 7.5, simulated gastric or intestinal fluid (with or without enzymes), water, and surfactants (with or without acids or buffers) such as polysorbate 80, sodium lauryl sulfate, and bile salts. Biorelevant dissolution media can contain a complex of bile salts (sodium taurocholate) and phospholipids (lecithin) in a 4:1 molar ratio as described in E. Galia, et al., Evaluation of Various Dissolution Media for Predicting In Vivo Performance of Class I and II Drugs. Pharmaceutical Research (1998) 15(5): 698-705. In some embodiments, the dissolution medium can be a Fasted State Simulated Intestinal Fluid (FaSSIF, composition: 3 mM sodium taurocholate, 0.75 mM lecithin, 28.65 mM $NaH_2PO_4$, 8.7 mM NaOH, 105.85 mM NaCl, pH 6.5) to simulate the contents of the human small intestine before a meal. In some embodiments, the dissolution medium can be a Fed State Simulated Intestinal Fluid (FeSSIF, composition: 15 mM sodium taurocholate, 3.75 mM lecithin, 144 mM $CH_3COOH$, 101 mM NaOH, 173 mM NaCl, pH 5.0) to simulate the contents of the human small intestine after a meal. In some embodiments, the dissolution medium can be a Fasted State Simulated Gastric Fluid (FaSSGF, composition: 0.08 mM sodium taurocholate, 0.02 mM lecithin, 34.2 mM NaCl, pH 1.6) to simulate the contents of gastric juice in an empty stomach. In aspects where the dissolution medium is the buffer solution, the medium can be adjusted so that its pH is within 0.05 unit of pH 1.2, pH 1.6, pH 5, pH 6.5, pH 6.8, pH 7.2, or pH 7.5. Suitable pH includes from about pH 1.0 to about pH 7.5. Cell compatible simulated intestinal fluids, $FaSSIF_{cell}$ and $FeSSIF_{cell}$, can be prepared based on Hank's Balance Salt Solution (HBSS, composition: 1.26 mM calcium chloride ($CaCl_2$), 5.33 mM potassium chloride (KCl), 0.44 mM potassium phosphate monobasic ($KH_2PO_4$), 0.50 mM Magnesium chloride ($MgCl_2$), 0.41 mM magnesium sulfate ($MgSO_4$), 138 mM sodium chloride (NaCl), 4.00 mM sodium bicarbonate ($NaHCO_3$), 0.30 mM sodium phosphate dibasic ($Na_2HPO_4$), and 25 mM glucose) by adding sodium taurocholate and lecithin. $FaSSIF_{cell}$ can contain 3 mM sodium taurocholate and 0.75 mM lecithin. The pH of $FaSSIF_{cell}$ can be adjusted with HEPES to 6.5. $FeSSIF_{cell}$ can contain 15 mM sodium taurocholate and 3.75 mM lecithin. The pH of $FaSSIF_{cell}$ can be adjusted with HEPES to 5.0.

Generally, in clinical pharmacokinetic studies, a tablet, capsule, or other formulation (such as liquids, solids, suspensions, or gels) are taken with one glass of water (i.e. 8 ounces, or ~250 mL). Accordingly, in some embodiments, the system can be configured to hold about 250 mL of dissolution medium to recapitulate the in vivo dose/volume ratio. The dissolution vessel can be configured to hold a volume of dissolution medium about equal to the average volume of fluid in the stomach and/or intestine of a human. In some aspects, the dissolution vessel can be configured to hold a volume of dissolution medium that is about equal to the average volume of gastric and/or intestinal fluid in a human in a fasting state. In other aspects, the dissolution vessel can be configured to hold a volume of dissolution medium that is about equal to the average volume of gastric and/or intestinal fluid in a human in a fed state. Thus, the system can mimic the in vivo conditions and predict dissolution and absorption in a human in either fasting or fed conditions. The dissolution vessel can be configured to hold a volume of dissolution medium that is about equal to the average volume of gastric and/or intestinal fluid in an adult human. For example, and without intending to be limiting, the fluid volume in the stomach in a fasted state and a fed state can be around 300 mL and 500 mL, respectively, and the fluid volume in the small intestine in a fasted state and a fed state can be around 200 mL and 1,000 mL, respectively. In some aspects, the dissolution vessel can be configured to hold about 250 mL. In some aspects, the dissolution vessel can be configured to hold about 300 mL. In some aspects, the dissolution vessel can be configured to hold about 400 mL. In some aspects, the dissolution vessel can be configured to hold about 500 mL. In some aspects, the dissolution vessel can be configured to hold about 750 mL. In some aspects, the dissolution vessel can be configured to hold about 1,000 mL. Alternatively, the dissolution vessel can be configured to hold a volume of dissolution medium that is about equal to the average volume of gastric and/or intestinal fluid in a non-adult human. Non-adult humans include, for example, new-born, pediatric, children, and teenagers. In some aspects, for example, the dissolution vessel can be configured to hold about 100 mL. In some aspects, the dissolution vessel can be configured to hold about 150 mL. In some aspects, the dissolution vessel can be configured to hold about 200 mL.

The dissolution vessel can be configured to hold from about 100 mL to about 1,000 mL of dissolution medium. In some aspects, the dissolution vessel can be configured to hold about 100 mL to about 750 mL. In some aspects, the dissolution vessel can be configured to hold about 100 mL to about 500 mL. In some aspects, the dissolution vessel can be configured to hold about 100 mL to about 400 mL. In some aspects, the dissolution vessel can be configured to hold about 100 mL to about 250 mL. In some aspects, the dissolution vessel can be configured to hold about 250 mL to about 1,000 mL. In some aspects, the dissolution vessel can be configured to hold about 250 mL to about 750 mL. In some aspects, the dissolution vessel can be configured to hold about 250 mL to about 500 mL. In some aspects, the dissolution vessel can be configured to hold about 250 mL to about 400 mL. In some aspects, the dissolution vessel can be configured to hold about 500 mL to about 1,000 mL. In some aspects, the dissolution vessel can be configured to hold from about 500 mL to about 750 mL.

The disclosed systems comprise at least one device. In some aspects, the system can have 1 device. In other aspects, the system can have 2 devices. In other aspects, the system can have 3 devices. In other aspects, the system can have 4 devices. In other aspects, the system can have 5 devices. In yet other aspects, the system can have more than 5 devices.

Any of the devices disclosed herein can be incorporated into the disclosed systems. Accordingly, the systems can have at least one device having any of the previously disclosed characteristics, including, but not limited to, shapes, volumes of permeability medium, cell/tissue/artificial membrane types, etc. For example, in some embodiments of the disclosed systems, the at least one device can be configured to hold from about 3 mL to about 10 mL volume of a permeability medium.

The volume of permeability medium and the volume of dissolution medium can be such that the media are at approximately the same level within the system. "Same level" is intended to mean an approximately equal height of permeability medium and dissolution medium when viewing the system from a cross-sectional view.

The at least one device can have a stirring blade within the reservoir. In some embodiments, the system can have one device, wherein the one device can have a stirring blade in the reservoir. In other embodiments, the system can have more than one device, wherein at least one of said more than one device can have a stirring blade within the reservoir. In yet other embodiments, the system can have more than one device, wherein all of said devices have a stirring blade within the reservoir.

The system can have a lid. In some embodiments, the at least one device is configured to be attached to the lid.

The system is configured to assess dissolution rates of intact tablets, capsules, or other formulations, or portions of the tablets, capsules, or other formulations, and cellular absorption and membrane permeability of active ingredients from the intact tablets, capsules, or other formulations, or portions of the tablets, capsules, or other formulations. Accordingly, the system avoids the need to crush tablets, capsules, or other formulations. The ability to assess intact tablets, capsules, and other formulations is extremely valuable, as administration of a crushed tablet, capsule, or other formulation does not mimic the sequence of events that take place in the stomach, and can decrease the likelihood that the results will correlate to in vivo absorption. In some embodiments, the intact tablet, capsule, or other formulation is a clinically sized tablet, capsule, or other formulation. As used herein, "portions thereof" is intended to mean less than the whole drug tablet, capsule, or other formulation, wherein the less than whole drug tablet, capsule, or other formulation is intact. Thus, the systems can be used to assess the dissolution rate, cellular absorption, and/or membrane absorption of less than whole, but still intact, drug tablets, capsules, and other formulations.

By integrating the disclosed devices into a dissolution vessel, it will be possible to develop a better understanding of the interaction between drug product dissolution and active ingredient absorption and permeability. This system not only connects the dissolution and permeability tests, but allows the addition of physiological components to the donor compartment (dissolution vessel) (e.g., bile acids) and the receiver compartment (device chamber) (e.g., plasma proteins).

Methods for Concomitant Measuring of Dissolution, Absorption and Permeation of a Drug Also provided herein are methods for concomitant measuring of dissolution, absorption and/or permeation of a drug comprising: adding an intact drug tablet, capsule, or other formulation, or a portion of the drug tablet, capsule, or other formulation, to the dissolution vessel of any one of the systems disclosed above, wherein the dissolution vessel contains a dissolution medium and the device contains a permeability medium, and wherein the permeability barrier contains a layer of cells, a layer of tissue, or a layer of artificial membrane; mixing the dissolution medium; withdrawing a sample from the dissolution vessel, the device, or both; and analyzing the sample from the dissolution vessel, the device, or both.

Any of the above disclosed systems and devices can be used in the disclosed methods. Accordingly, the disclosed methods can have a system with device(s) having any of the above disclosed characteristics including, but not limited to, volume of dissolution medium, volume of permeability medium, shape of the device components, cell/tissue/artificial membrane type, etc., incorporated therein. For example, the methods comprise adding an intact drug tablet, capsule, or other formulation, or a portion of the tablet, capsule, or other formulation, to the dissolution vessel of any one of the disclosed systems, wherein the dissolution vessel contains a dissolution medium. Suitable dissolution mediums include those disclosed above. Similarly, the device contains a permeability medium. Suitable permeability mediums include those disclosed above.

The dissolution medium, permeability medium, or both can contain components that mimic physiological conditions. In some aspects, for example, bile salts (sodium taurocholate) and phospholipids (lecithin) can be added to the dissolution medium. In some aspects, plasma proteins (bovine serum albumin) can be added to the permeability medium.

The methods comprise adding an intact drug tablet, capsule, or other formulation, or a portion of the tablet, capsule, or other formulation, to the dissolution vessel. In some embodiments, a single intact drug tablet, capsule, or other formulation, or a portion of the tablet, capsule, or other formulation, can be added to the dissolution vessel. In other embodiments, multiple intact drug tablets, capsules, or other formulations, or a portion of the tablets, capsules, or other formulations, can be added to the dissolution vessel. The number of intact drug tablets, capsules, or other formulations, or portions of the tablets, capsules, or other formulations, added to the dissolution vessel depends, in part, on the volume of dissolution medium present within the vessel and the dose of the drug tablet, capsule, or other formulation. In some embodiments, the recommended dose of the drug tablet, capsule, or other formulation is added to the dissolution vessel with the recommended amount of fluid to be consumed with the drug. For example, the dissolution vessel can contain about 250 mL of dissolution medium. In such aspects, if it is recommended that the drug be taken with 250 mL of fluid, then a single intact drug tablet, capsule, or other formulation can be added to the dissolution vessel. Alternatively, the dissolution vessel can contain more than 250 mL of dissolution medium. In such aspects, the amount of intact drug tablet, capsule, or other formulation can be scaled to maintain physiological conditions. If the dissolution vessel contains 500 mL of dissolution medium, for example, and it is recommended that the drug be taken with 250 mL of fluid, the method can comprise adding 2 intact drug tablets, capsules, or other formulations to the dissolution vessel. If the dissolution vessel contains 750 mL of dissolution medium and it is recommended that the drug be taken with 250 mL of fluid, the method can comprise adding 3 intact drug tablets, capsules, or other formulations to the dissolution vessel. If the dissolution vessel contains 1,000 mL of dissolution medium and it is recommended that the drug be taken with 250 mL of fluid, the method can comprise adding 4 intact drug tablets, capsules, or other formulations to the dissolution vessel. And so on.

The intact drug tablet, capsule, or formulation, or portion of the tablet, capsule, or other formulation, can be added directly to the dissolution vessel. For example, the intact drug table, capsule, or formulation, or portions thereof, can be placed into the dissolution vessel so that the drug sits on the bottom of the vessel. Alternatively, in embodiments wherein the system contains a stirring cage as a stirring apparatus, the intact tablet, capsule, or formulation, or portions thereof, can be placed within the stirring cage.

The dissolution testing can be carried out in one-stage or two-stage configurations. In a one-stage configuration, the intact drug tablet, capsule, or other formulation, or portions of the tablet, capsule, or other formulation, can be added directly to the dissolution vessel containing simulated intestinal fluids having a pH ranging from 5.0 to 6.5 (exemplary simulated intestinal fluids are described previously herein). In a two-stage configuration, the intact drug tablet, capsule, or other formulation, or portions of the tablet, capsule, or other formulation, can be added directly to the dissolution vessel initially containing simulated gastric fluids having a pH ranging from 1.0 to 2.0 (exemplary simulated gastric fluids are described previously herein), and after a preselected duration of 10 to 60 min, the dissolution media is adjusted to simulated intestinal fluids having a pH ranging from 5.0 to 6.5.

The methods comprise mixing the dissolution medium. The mixing step is performed using a stirring apparatus present within the system. The system can contain, for example, a stirring blade, a stirring cage, a magnetic stirring bar, or any combination thereof as the stirring apparatus. The method comprises operating any of these stirring apparatuses at a suitable speed in order to mix the dissolution medium. Suitable speeds include, but are not limited to, 25 rpm, 50 rpm, 75 rpm, and 100 rpm.

The systems contain at least two compartments: a donor compartment comprising the dissolution vessel containing a dissolution medium; and a receiver compartment comprising the device containing a permeability medium. Upon addition of an intact tablet, capsule or other formulation, or a portion of the tablet, capsule, or other formulation, to the system, the disclosed methods enable the concomitant measuring of: dissolution and permeation across a cell, tissue, or artificial membrane layer; dissolution and cellular absorption; and dissolution, cellular absorption and permeation across a cell, tissue, or artificial layer.

The methods can comprise measuring dissolution and permeation. In some embodiments, the methods comprise withdrawing a sample from the dissolution vessel, the device, or both and analyzing the sample from the dissolution vessel, the device, or both. The amount of active ingredient in the sample from the dissolution vessel indicates a level of dissolution, whereas the amount of active ingredient in the sample from the device indicates a level of permeation.

The methods can also comprise measuring dissolution and absorption. In some embodiments, the methods comprise withdrawing a sample from the dissolution vessel, the device or both and analyzing the sample from the dissolution vessel, the device, or both. In some embodiments, the methods can further comprise comparing an amount of active ingredient in the sample from the dissolution vessel and an amount of active ingredient from the sample from the device with a total amount of active ingredient within the drug. The amount of active ingredient in the sample from the dissolution vessel indicates a level of dissolution, and the difference in the amount of active ingredient in the sample from the dissolution vessel and the sample from the device compared to a total amount of active ingredient within the drug indicates a level of absorption.

In other embodiments, the system can comprise two or more devices, wherein a first device has a cell layer, tissue, or artificial membrane layer within the permeation barrier and a second device does not have a cell layer, tissue layer, or artificial membrane layer within the permeation barrier. The method can comprise withdrawing a sample from the dissolution vessel and the first and second device and comparing an amount of active ingredient in the sample from the first device and an amount of active ingredient from the sample from the second device. The amount of active ingredient in the sample from the dissolution vessel indicates a level of dissolution. The difference in the amount of active ingredient in the sample from the first device and the sample from the second device indicates a level of absorption.

In yet other embodiments, the methods can further comprise isolating the cell layer, tissue layer, or artificial membrane layer from the permeability barrier and measuring the amount of active ingredient within the cell layer, tissue layer, or artificial membrane layer.

Samples can be withdrawn from the dissolution vessel, the device, or both at any suitable time point before and/or after the intact capsule, tablet, or other formulation, or a portion of the capsule, tablet, or other formulation, is added to the dissolution vessel. Samples can be withdrawn at, for example, 1 minute intervals, 5 minute intervals, 10 minute intervals, 15 minute intervals, 20 minute intervals, 25 minute intervals, 30 minute intervals, hour intervals, or any combination thereof.

The methods can be performed for about 2 hours to about 4 hours. In some embodiments, the methods can be performed for about 2 hours. In other embodiments, the methods can be performed for about 3 hours. In yet other embodiments, the methods can be performed for about 4 hours.

In some aspects, the method comprises withdrawing a sample from the dissolution vessel and/or the device at 1 minute intervals. In some aspects, the method comprises withdrawing a sample from the dissolution vessel and/or the device at 5 minute intervals. In some aspects, the method comprises withdrawing a sample from the dissolution vessel and/or the device at 10 minute intervals. In some aspects, the method comprises withdrawing a sample from the dissolution vessel and/or the device at 15 minute intervals. In some aspects, the method comprises withdrawing a sample from the dissolution vessel and/or the device at 20 minute intervals. In some aspects, the method comprises withdrawing a sample from the dissolution vessel and/or the device at 25 minute intervals. In some aspects, the method comprises withdrawing a sample from the dissolution vessel and/or the device at 30 minute intervals. In some aspects, the method comprises withdrawing a sample from the dissolution vessel and/or the device at hour intervals. In some aspects, the method comprises withdrawing a sample from the dissolution vessel and/or the device at any combination of the above intervals.

Samples can be withdrawn from the dissolution vessel and the device at the same time intervals. Alternatively, samples can be withdrawn from the dissolution vessel and the device at different time intervals. In other aspects, some samples can be withdrawn from the dissolution vessel and the device at the same time intervals, while yet other samples can be withdrawn from the dissolution vessel and the device at different time intervals. For example, and without intent to be limiting, the method can comprise withdrawing samples from the dissolution vessel at 1 minute intervals for the first 10 minutes, withdrawing samples from both the dissolution vessel and the device at 5 minute intervals for the next hour, and withdrawing samples from the device at 5 minute intervals for the next hour.

When a sample is withdrawn from the dissolution vessel, the device, or both, an equivalent volume of dissolution medium and/or permeability medium as that which was withdrawn can be added to the dissolution vessel and the device, respectively.

The withdrawn samples can be analyzed using a number of techniques known in the art. Suitable analyzing techniques include, but are not limited to, fluorescence detection, UV-visible (UV) spectrometry, liquid chromatography-UV (LC-UV), liquid chromatography-mass spectrometry (LC-MS), LC-MS/MS, radioactive scintillation counting, or any combination thereof.

In some embodiments, the methods can be used to measure absorption into, and/or permeation across, a single type of cell layer, tissue layer, or artificial membrane layer. For example, a system can contain one or more devices, wherein each device can contain the same cell layer, tissue layer, or artificial membrane layer. In other embodiments, the methods can be used to measure absorption into, and/or permeation across, more than one type of cell layer, tissue layer, or artificial membrane layer. For example, a system can contain two or more devices, wherein at least two of the devices can contain a different type of cell layer, tissue layer, or artificial membrane layer. Thus, the disclosed methods can be used to simultaneously measure absorption into, and permeability across, multiple cell, tissue, or artificial membrane types.

Suitable temperatures for performing the disclosed methods, include, but are not limited, to about 34° C. to about 41° C. In some aspects, the disclosed methods are performed at about 37° C.

EXAMPLES

Assembly and Use of the Disclosed Devices

The device(s) can be assembled as illustrated in FIG. 1, and each device can be attached to the vessel lid. Dissolution medium and permeability medium can be added to the dissolution vessel and permeability chamber, respectively, ensuring that the dissolution media and permeability media are at approximately the same level. The system can be equilibrated to 37±0.5° C. A drug dosage unit (drug tablet, capsule, or other formulation, or a portion of the tablet, capsule, or other formulation) can be placed into the dissolution medium, taking care to exclude air bubbles from the surface of the dosage unit, and the system can be immediately operated at the specified rates. Within a time interval specified, or at each of a number of times stated, a specimen can be withdrawn from the dissolution vessel at a zone midway between the surface of the dissolution medium and the top of the rotating blade or basket, and not less than 1 cm from the vessel wall. The vessel can be kept covered for the duration of the test. Within a time interval specified, or at each of a number of times stated, a specimen can be withdrawn from the permeability chamber at a middle zone of permeability medium. Where multiple sampling times are specified, the amounts withdrawn for analysis can be replaced with an equivalent volume of fresh (dissolution or permeability) medium at 37° C., or where it is shown that replacement of the medium is not necessary, the volume change can be factored into any subsequent analysis. The samples of dissolution medium and permeability medium can be analyzed using a suitable assay method.

Method for Concomitant Measuring of Dissolution and Absorption of a Drug

Materials

Propranolol tablet, 10 mg strength, was manufactured by Qualitest Pharmaceuticals (Huntsville, Ala.). Warfarin tablet, 1 mg strength, was manufactured by Barr Laboratories Inc. (Champaign, Ill.). C2BBel [clone of Caco-2 cells] were obtained from American Type Culture Collection (ATCC® CRL-2102™) (Manassas, Va.). Sodium taurocholate and D-glucose were obtained from Sigma-Aldrich® (St. Louis, Mo., USA). Lecithin was obtained from Fisher Scientific® (Pittsburg, Pa., USA). 4-(2-hydroxyethyl)-1-piperazineethanesulfonic acid (HEPES), Hanks' balanced salt solution supplemented with 15 mM glucose (HBSSg), Dulbecco's modified Eagle's medium (DMEM), Dulbecco's phosphate-buffered saline (DPBS), fetal bovine serum (FBS), penicillin-streptomycin mixture, non-essential amino acids, sodium pyruvate, trypsin, G418 and L.M.P. agarose were obtained from Life Technologies (Grand Island, N.Y., USA). Sodium butyrate was purchased from Alfa Aesar® (Ward Hill, Mass., USA). Rat tail collagen type 1 was purchased from BD Gentest™ (Woburn, Mass., USA). Costar® Snapwell plates (12-well format, 1.13 cm$^2$ insert area, 0.4 μm pore size) were purchased from Corning® Life Sciences (Corning®, NY, USA). Formic acid (88%, v/v) was purchased from JTBaker® (Center Valley, Pa., USA). Methanol, acetonitrile, and dimethyl sulfoxide (DMSO) were purchased from EMD Millipore (Billerica, Mass., USA).

Caco-2 Cell Culture

Caco-2 cells were maintained in DMEM containing 10% FBS, 1% NEAA (non-essential amino acids) solution, 4 mM L-glutamine, 1 mM sodium pyruvate, 100 IU/mL penicillin, and 100 μg/mL streptomycin in a humidified incubator (37° C., 5% $CO_2$). The culture medium was changed three times weekly, and cell growth was observed by light microscopy. When the stock cultures were ~80% confluent, the cells were harvested by trypsinization and seeded onto collagen-coated polycarbonate membranes in Costar® Snapwell plates (1.13 cm$^2$ insert area, 0.4 μm pore size; Corning® Life Sciences, Corning®, NY) to grow cell monolayers for the permeability studies. The seeding density was 60,000 cells/cm$^2$. The plates were placed in a humidified incubator (37° C., 5% $CO_2$), and the culture medium was changed every other day until use (20 to 28 days after seeding).

Concomitant Measurement of Dissolution and Permeation

The disclosed systems (IDAS—in vitro dissolution absorption systems) enable one to simultaneously assess oral drug absorption as well as dissolution and permeation processes of drugs. A system comprising two devices for assessing drug dissolution and absorption (as exemplified in FIG. 3) was used in these studies. Caco-2 cell monolayers were mounted in the interface between the dissolution vessel and the IDAS. Hanks balanced salts solution supplemented with 15 mM glucose was used as the basal solution. Fasted state simulated intestinal fluid (FaSSIF) was used as the dissolution medium, which was prepared by supplementing basal solution HBSSg with 3 mM sodium taurocholate and 0.75 mM lecithin and adjusting the pH to 6.5 with HEPES. 500 mL of dissolution medium was added to the dissolution vessel. HBSSg containing 4.5% (w/v) bovine serum albumin (pH adjusted to 7.4) was used as the permeation medium, 8 ml of which was added to each device. The system was pre-warmed for 10 minutes to 37° C. and the dissolution media was consistently stirred at 50 RPM. At time zero, two tablets of drug (propranolol or warfarin) were added to the dissolution vessel. At pre-selected time points (i.e. 5, 15, 30, 60, 90, and 120 mM), samples were collected from the dissolution vessel and each device. At each sampling time point, 0.1 mL of sample was collected from the dissolution vessel and passed through 0.2 μm Millex-FG syringe filter unit (EMD Millipore, Billerica, Mass.) to remove undissolved residues. At each sampling time point, 0.5 mL of sample was collected from each device and the same volume (0.5 mL) of fresh permeation medium was added back into the device.

Sample Analyses

Drug concentrations were determined using liquid chromatography with triple quadruple tandem mass spectrometry (LC-MS/MS) methods. The high-performance liquid chromatography equipment consisted of a LEAP CTC HTS PAL autosampler (LEAP Technologies, Carrboro, N.C.) and Agilent 1100 pumps (Agilent Technologies, Santa Clara, Calif.). Chromatography was performed at an ambient temperature using a 30×2.1 mm i.d., 3 μm Thermo Hypersil BDS C18 column (Thermo Fisher Scientific) with a guard column. The mobile phase buffer was 25 mM ammonium formate buffer, pH 3.5; the aqueous phase consisted of 90% deionized water and 10% mobile phase buffer (v/v); the organic phase consisted of 90% acetonitrile and 10% mobile phase buffer. The gradient started at 5% organic phase and changed linearly over 1.5 min to 100% organic phase at 250 μL/min flowrate. The injection volume was 10 μL, and the total run time was 3.5 min. Mass spectrometry was performed on a Sciex API4000™ triple quadruple mass spectrometer in the multiple reaction monitoring modes using a Turbo IonSpray interface (Applied Biosystems®, Foster City, Calif.).

Results

Figure 4A:
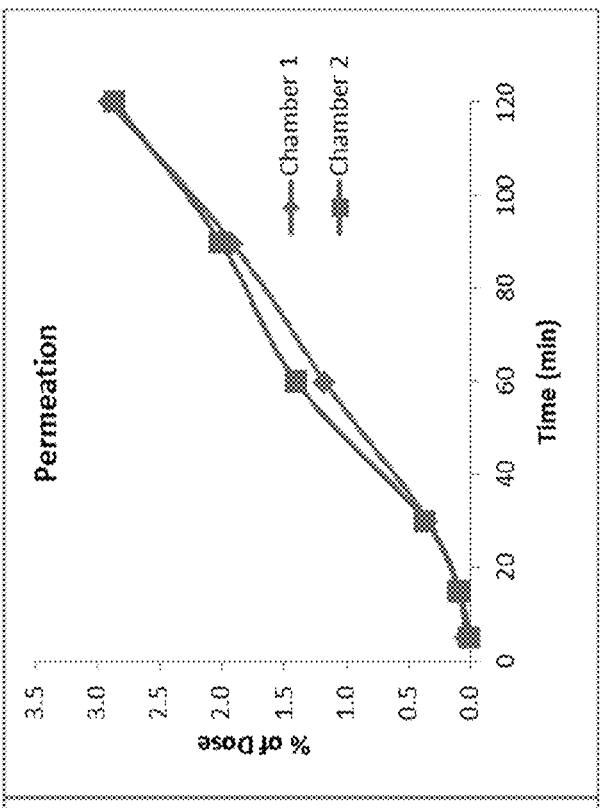
FIG. 4A and FIG. 4B illustrate exemplary dissolution (FIG. 4A) and permeation (FIG. 4B) profiles of propranolol tablets in the disclosed systems.
Figure 4B:
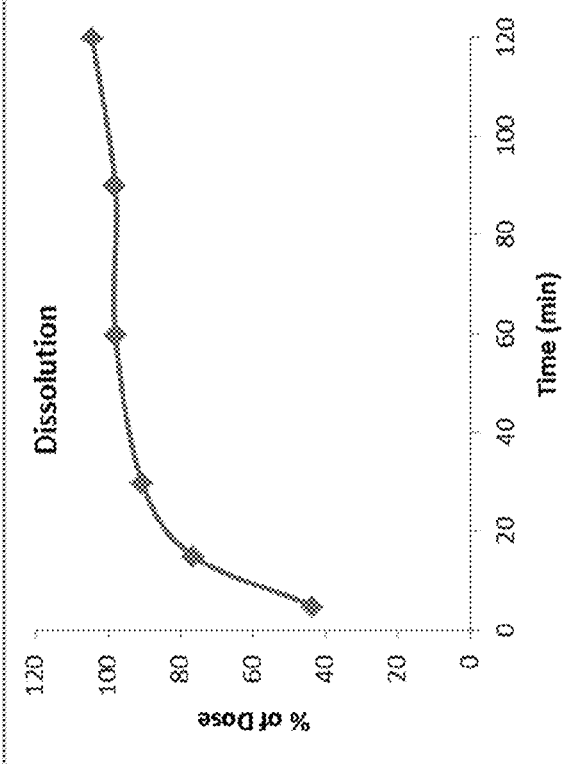

Simultaneously measured dissolution and permeation results of propranolol tablets are listed in Table 1 and graphically illustrated in FIG. 4A and FIG. 4B, respectively.

TABLE 1

Dissolution and permeation results of propranolol tablets

| Time (min) | Dissolved Drug (μM) | Permeated Drug (μM) | | Dissolution (% of dose) | Permeation (% of dose) | |
|---|---|---|---|---|---|---|
| | | R 1 | R 2 | | R 1 | R 2 |
| 5 | 16.1 | 0.0162 | 0.00309 | 43.5 | 0.0438 | 0.0084 |
| 15 | 28.3 | 0.034 | 0.0351 | 76.5 | 0.0946 | 0.0954 |
| 30 | 33.5 | 0.125 | 0.135 | 90.6 | 0.346 | 0.371 |
| 60 | 36.2 | 0.424 | 0.511 | 97.9 | 1.18 | 1.41 |
| 90 | 36.2 | 0.674 | 0.702 | 97.9 | 1.92 | 2.01 |
| 120 | 38.6 | 0.996 | 0.971 | 104 | 2.91 | 2.86 |

Figure 5A:
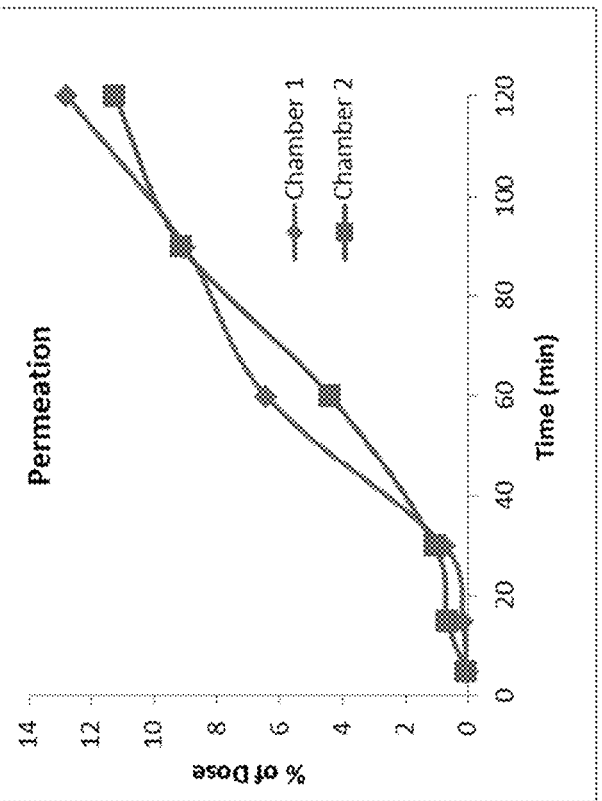
FIG. 5A and FIG. 5B illustrate exemplary dissolution (FIG. 5A) and permeation (FIG. 5B) profiles of warfarin tablets in the disclosed systems.
Figure 5B:
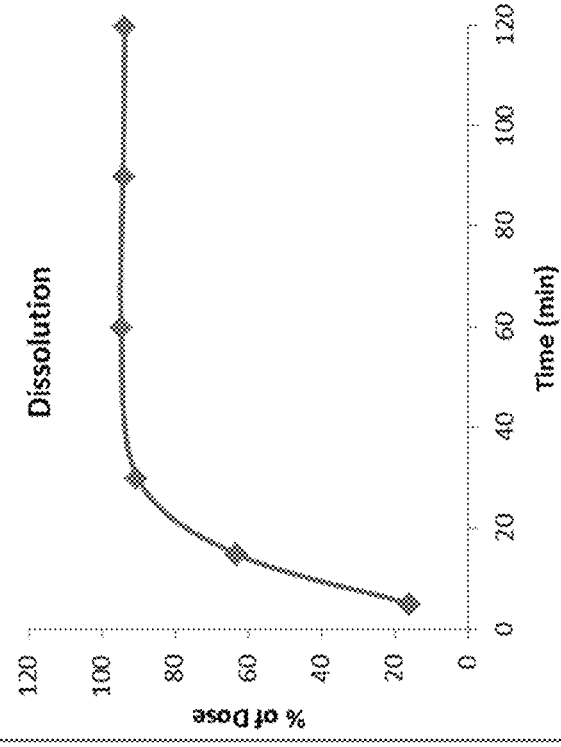

Simultaneously measured dissolution and permeation results of warfarin tablets are listed in Table 2 and graphically illustrated in FIG. 5A and FIG. 5B, respectively.

TABLE 2

Dissolution and permeation results of warfarin tablets

| Time (min) | Dissolved Drug (μM) | Permeated Drug (μM) | | Dissolution (% of dose) | Permeation (% of dose) | |
|---|---|---|---|---|---|---|
| | | R 1 | R 2 | | R 1 | R 2 |
| 5 | 0.523 | 0.00199 | 0.00239 | 15.9 | 0.060 | 0.0724 |
| 15 | 2.09 | 0.00591 | 0.0223 | 63.4 | 0.183 | 0.680 |
| 30 | 2.98 | 0.025 | 0.0338 | 90.3 | 0.773 | 1.07 |
| 60 | 3.12 | 0.211 | 0.142 | 94.7 | 6.46 | 4.41 |
| 90 | 3.1 | 0.283 | 0.289 | 94.2 | 9.04 | 9.14 |
| 120 | 3.08 | 0.389 | 0.341 | 93.7 | 12.8 | 11.3 |

The devices, systems, and methods disclosed herein have a number of uses, including: facilitating the understanding of the relationship between drug-product dissolution and active ingredient absorption and permeability; reducing the number of dog studies, which are time-consuming and pose ethical concerns, for screening formulations of new molecular entities; optimizing formulations in vitro to reduce the number of clinical trials needed to demonstrate bioequivalence between generic and innovator or reference drug products; and evaluating the effect of food on the oral absorption of BCS Class 2 (low solubility, high permeability) drugs to satisfy the requirements of the US FDA, as previous studies have found that the dog, the most commonly used model, is a bad predictor of food effect in humans.

Those skilled in the art will appreciate that numerous changes and modifications can be made to the preferred embodiments and that such changes and modifications can be made without departing from the spirit of the disclosed devices, systems, and methods. It is, therefore, intended that the appended claims cover all such equivalent variations as fall within the true spirit and scope of the devices, systems, and methods.

The disclosures of each patent, patent application, and publication cited or described in this document are hereby incorporated herein by reference, in its entirety.

Embodiments

The following list of embodiments is intended to complement, rather than displace or supersede, the previous descriptions.

Embodiment 1. A device for assessing drug dissolution, absorption and permeation comprising:
  a chamber comprising
    a reservoir having a bottom, at least one side wall, and a hollow interior, the side wall having an opening; and
    an extension having at least one side wall, a distal end, a proximal end, and a hollow interior, wherein the distal end and the proximal end are open, and wherein the proximal end is attached to the side wall at the opening;
  a permeability barrier having a least one side wall, an open distal end, and a proximal end, wherein the permeability barrier is configured to hold cells, tissues, or artificial membranes and the proximal end of the permeability barrier is configured to contact the distal end of the extension; and
  a securing cap having at least one side wall, a distal end, a proximal end, and a hollow interior, wherein the distal end and proximal end are open and wherein the securing cap is configured to reversibly attach to the permeability barrier or the extension,
  wherein the securing cap, permeability barrier, and chamber are in fluid communication.

Embodiment 2. The device of embodiment 1, wherein the top of the reservoir is open.

Embodiment 3. The device of embodiment 1 or 2, wherein the extension is perpendicular to the reservoir.

Embodiment 4. The device of any one of the previous embodiments, further comprising a seal configured for insertion between the distal end of the extension and the proximal end of the permeability barrier.

Embodiment 5. The device of embodiment 4, wherein the seal is an O-ring.

Embodiment 6. The device of any one of the previous embodiments, wherein the permeability barrier is configured to hold a layer of cells.

Embodiment 7. The device of any one of the previous embodiments, wherein the permeability barrier is configured to hold a tissue layer.

Embodiment 8. The device of any one of the previous embodiments, wherein the permeability barrier is configured to hold an artificial membrane layer.

Embodiment 9. The device of any one of the previous embodiments, wherein the device is configured to receive a permeability medium.

Embodiment 10. A system for assessing drug dissolution, absorption, and permeation comprising:
at least one device of any one of embodiments 1-9;
a dissolution vessel configured to hold a dissolution medium; and
a stirring apparatus within the dissolution vessel;
wherein the system is configured to assess: dissolution rates of an intact drug tablet, capsule, or other formulation, or portions of the tablet, capsule, or other formulation; absorption of active ingredients from the tablet, capsule, or other formulation, or a portion of the tablet, capsule, or other formulation; and/or membrane permeability of active ingredients from the tablet, capsule, or other formulation, or a portion of the tablet, capsule, or other formulation.

Embodiment 11. The system of embodiment 10, the at least one device having a stirring blade within the reservoir.

Embodiment 12. The system of embodiment 10 or 11, wherein the stirring apparatus within the dissolution vessel is a stirring blade.

Embodiment 13. The system of any one of embodiments 10-12, wherein the stirring apparatus within the dissolution vessel is a stirring cage configured to hold the drug tablet, capsule, or other formulation.

Embodiment 14. The system of any one of embodiments 10-13, wherein the dissolution vessel is configured to hold from about 100 mL to about 1,000 mL of dissolution medium.

Embodiment 15. The system of any one of embodiments 10-14, wherein the at least one device is configured to hold from about 3 mL to about 10 mL volume of a permeability medium.

Embodiment 16. The system of any one of embodiments 10-15, further comprising a lid.

Embodiment 17. The system of embodiment 16, wherein the at least one device is configured to be attached to the lid.

Embodiment 18. A method for concomitant measuring of dissolution, absorption and/or permeation of a drug comprising:
adding an intact drug tablet, capsule, or other formulation, or a portion of the tablet, capsule, or other formulation, to the dissolution vessel of the system of any one of embodiments 10-17, wherein the dissolution vessel contains a dissolution medium and the device contains a permeability medium, and wherein the permeability barrier contains a layer of cells, a layer of tissue, or a layer of artificial membrane;
mixing the dissolution medium;
withdrawing a sample from the dissolution vessel, the device, or both; and
analyzing the sample from the dissolution vessel, the device, or both.

Embodiment 19. The method of embodiment 18, wherein the drug tablet, capsule, or other formulation is intact.

Embodiment 20. The method of embodiment 18 or 19, wherein the method comprises measuring dissolution and permeation.

Embodiment 21. The method of embodiment 20, wherein an amount of active ingredient in the sample from the dissolution vessel indicates a level of dissolution, and an amount of active ingredient in the sample from the device indicates a level of permeation.

Embodiment 22. The method of embodiment 18 or 19, wherein the method comprises measuring dissolution and absorption.

Embodiment 23. The method of embodiment 22, further comprising comparing an amount of active ingredient in the sample from the dissolution vessel and an amount of active ingredient from the sample from the device with a total amount of active ingredient within the drug.

Embodiment 24. The method of embodiment 23, wherein an amount of active ingredient in the sample from the dissolution vessel indicates a level of dissolution, and a difference in the amount of active ingredient in the sample from the dissolution vessel and the sample from the device compared to the total amount of active ingredient within the drug indicates a level of absorption.

Embodiment 25. The method of embodiment 22, wherein the system has two or more devices, wherein a first device has a cell layer, tissue layer, or artificial membrane layer within the permeation barrier and a second device does not have a cell layer, tissue layer, or artificial membrane layer within the permeation barrier, and wherein the method comprises withdrawing a sample from the first device and a sample from the second device and comparing an amount of active ingredient in the sample from the first device and an amount of active ingredient from the sample from the second device.

Embodiment 26. The method of embodiment 25, wherein an amount of active ingredient in the sample from the dissolution vessel indicates a level of dissolution, and a difference in the amount of active ingredient in the sample from the first device and the amount of active ingredient from the sample from the second device indicates a level of absorption.

Embodiment 27. The method of any one of embodiment 18-26, further comprising isolating the cell layer, tissue layer, or artificial membrane layer from the permeability barrier and measuring an amount of active ingredient within the cell layer, tissue layer, artificial membrane layer.

What is claimed:

1. A device for assessing drug dissolution, absorption and permeation comprising:
a chamber comprising
a reservoir having a bottom, at least one side wall, and a hollow interior, the side wall having an opening; and
no more than one extension having at least one side wall, a single distal end, a single proximal end, and a hollow interior, wherein the distal end and the proximal end are open, and wherein the proximal end is attached to the side wall at the opening;
a permeability barrier having a least one side wall, an open distal end, and a proximal end, wherein the permeability barrier is configured to hold a layer of cells, a tissue layer, or a layer of an artificial membrane and the proximal end of the permeability barrier is configured to contact the distal end of the extension; and a securing cap having at least one side wall, a distal end, a proximal end, and a hollow interior, wherein the distal end and proximal end are open and wherein the securing cap is configured to reversibly attach to the permeability barrier or the extension, wherein the securing cap, permeability barrier, and chamber are in fluid communication.

2. The device of claim 1, wherein the top of the reservoir is open.

3. The device of claim 1, wherein the extension is perpendicular to the reservoir.

4. The device of claim 1, further comprising a seal configured for insertion between the distal end of the extension and the proximal end of the permeability barrier.

5. The device of claim 4, wherein the seal is an O-ring.

6. The device of claim 1, wherein the permeability barrier is configured to hold a layer of cells.

7. The device of claim 1, wherein the permeability barrier is configured to hold a tissue layer.

8. The device of claim 1, wherein the permeability barrier is configured to hold an artificial membrane layer.

9. The device of claim 1, wherein the device is configured to receive a permeability medium.

10. A system for assessing drug dissolution, absorption, and permeation comprising:
the device of claim 1, wherein the permeability barrier of the device contains a layer of cells, a tissue layer, or a layer of artificial membrane;
a dissolution vessel containing a volume of a dissolution medium about equal to the average volume of fluid in a human's gastrointestinal tract; and
a stirring apparatus within the dissolution vessel;
wherein the system is configured to assess: dissolution rates of an intact clinical size tablet, capsule, or other formulation, or portions of the tablet, capsule, or other formulation; absorption of active ingredients from the tablet, capsule, or other formulation, or a portion of the tablet, capsule, or other formulation; and/or membrane permeability of active ingredients from the tablet, capsule, or other formulation, or a portion of the tablet, capsule, or other formulation.

11. The system of claim 10, wherein the device has a stirring blade within the reservoir.

12. The system of claim 10, wherein the stirring apparatus within the dissolution vessel is a stirring blade.

13. The system of claim 10, wherein the stirring apparatus within the dissolution vessel is a stirring cage configured to hold the drug tablet, capsule, or other formulation.

14. The system of claim 10, wherein the dissolution vessel is configured to hold from about 100 mL to about 1,000 mL of dissolution medium.

15. The system of claim 10, wherein the device is configured to hold from about 3 mL to about 10 mL volume of a permeability medium.

16. The system of claim 10, further comprising a lid.

17. The system of claim 16, wherein the device is configured to be attached to the lid.

18. The system of claim 10, wherein the dissolution medium comprises a Fasted State Simulated Intestinal Fluid, a Fed State Simulated Intestinal Fluid, a Fasted State Simulated Gastric Fluid, cell compatible simulated intestinal fluids, or a biorelevant dissolution media containing bile acids and phospholipids.

19. The system of claim 10, wherein the layer of cells comprise a layer of epithelial cells.

20. A method for concomitant measuring of dissolution, absorption and/or permeation of a drug comprising:
adding an intact drug tablet, capsule, or other formulation, or a portion of the tablet, capsule, or other formulation, to the dissolution vessel of the system of claim 10, wherein the dissolution vessel contains a dissolution medium and the device contains a permeability medium, and wherein the permeability barrier contains a layer of cells, a layer of tissue, or a layer of artificial membrane;
mixing the dissolution medium;
withdrawing a sample from the dissolution vessel, the device, or both; and
analyzing the sample from the dissolution vessel, the device, or both.

21. The method of claim 20, wherein the drug tablet, capsule, or other formulation is intact.

22. The method of claim 20, wherein the method comprises measuring dissolution and permeation.

23. The method of claim 22, wherein an amount of active ingredient in the sample from the dissolution vessel indicates a level of dissolution, and an amount of active ingredient in the sample from the device indicates a level of permeation.

24. The method of claim 20, wherein the method comprises measuring dissolution and absorption.

25. The method of claim 24, further comprising comparing an amount of active ingredient in the sample from the dissolution vessel and an amount of active ingredient from the sample from the device with a total amount of active ingredient within the drug.

26. The method of claim 25, wherein an amount of active ingredient in the sample from the dissolution vessel indicates a level of dissolution, and a difference in the amount of active ingredient in the sample from the dissolution vessel and the sample from the device compared to the total amount of active ingredient within the drug indicates a level of absorption.

27. The method of claim 24, wherein the system has two or more devices, wherein a first device has a cell layer, tissue layer, or artificial membrane layer within the permeation barrier and a second device does not have a cell layer, tissue layer, or artificial membrane layer within the permeation barrier, and wherein the method comprises withdrawing a sample from the first device and a sample from the second device and comparing an amount of active ingredient in the sample from the first device and an amount of active ingredient from the sample from the second device.

28. The method of claim 27, wherein an amount of active ingredient in the sample from the dissolution vessel indicates a level of dissolution, and a difference in the amount of active ingredient in the sample from the first device and the amount of active ingredient from the sample from the second device indicates a level of absorption.

29. The method of claim 20, further comprising isolating the cell layer, tissue layer, or artificial membrane layer from the permeability barrier and measuring an amount of active ingredient within the cell layer, tissue layer, or artificial membrane layer.

* * * * *